(12) United States Patent
Mannschedel et al.

(10) Patent No.: US 8,227,018 B2
(45) Date of Patent: Jul. 24, 2012

(54) DENTAL POST

(75) Inventors: Werner Mannschedel, Langenau (DE);
Ralf Bohner, Kriessern (CH); Barbara Muller, Langenau (DE)

(73) Assignee: Coltene Whaledent AG, Altstatten (CH)

( * ) Notice: Subject to any disclaimer, the term of this patent is extended or adjusted under 35 U.S.C. 154(b) by 750 days.

(21) Appl. No.: 12/244,255

(22) Filed: Oct. 2, 2008

(65) Prior Publication Data

US 2010/0084778 A1 Apr. 8, 2010

(51) Int. Cl.
*A61K 6/083* (2006.01)

(52) U.S. Cl. .......... 427/2.26; 433/220; 433/228.1; 427/475; 427/485; 427/2.24; 427/2.27

(58) Field of Classification Search .......... 433/220, 433/228.1; 427/475, 485
See application file for complete search history.

(56) References Cited

U.S. PATENT DOCUMENTS

| | | | | |
|---|---|---|---|---|
| 5,629,050 A | * | 5/1997 | Silvis et al. | 427/475 |
| 5,741,139 A | * | 4/1998 | Sicurelli et al. | 433/220 |
| 6,224,377 B1 | * | 5/2001 | Bachmann et al. | 433/220 |
| 6,402,519 B1 | | 6/2002 | Nordin | |
| 2004/0002037 A1 | * | 1/2004 | Orlowski et al. | 433/220 |

FOREIGN PATENT DOCUMENTS

| | | |
|---|---|---|
| DE | 39 01 640 | 8/1989 |
| EP | 0 992 223 | 4/2000 |
| EP | 1 115 349 | 7/2001 |
| FR | 2 796 830 | 2/2001 |
| WO | 01/08590 | 2/2001 |

* cited by examiner

*Primary Examiner* — Dah-Wei Yuan
*Assistant Examiner* — Andrew Bowman
(74) *Attorney, Agent, or Firm* — Katten Muchin Rosenman LLP

(57) ABSTRACT

A method of manufacturing a dental post according to the present invention comprises the steps of: (i) overjacketing extrusion of at least one thermoplastic material over at least one filament or yarn, such that the thermoplastic material cross-sectionally enwraps the at least one filament or yarn; (ii) solidifying the extruded product of step (i); (iii) equipping the solidified extruded product of step (ii) with a surface texture, such that the thermoplastic wrapping is not modified in a way as to expose or damage the at least one filament or yarn.

Figure 1:
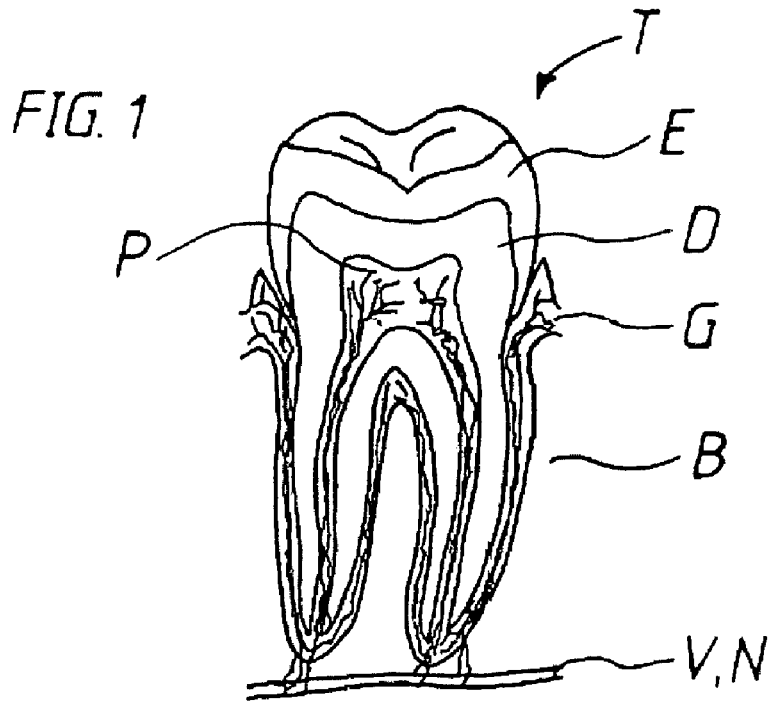

The invention allows for more flexibility in the manufacturing of dental posts, especially in generating surface textures of such dental posts.

2 Claims, 3 Drawing Sheets

DENTAL POST

The present invention pertains to the technical field of dental restorations, especially dental posts.

Dental posts are used frequently in dental restorations. Such dental posts are placed in a suitably prepared root canal, e.g. by means of a cement, with a head portion of the post extending over the prepared tooth. This head portion of the post is the basis for restoration of the damaged tooth.

A multitude of dental posts are available on the market today. Posts with a central filament or yarn, and a synthetic resin around this filament or yarn, are known e.g. from DE 39 01 640 A1.

Currently, such dental posts are most efficiently produced on a continuous basis by e.g. the pultrusion technique outlined in DE 39 01 640 A1. In brief, pultrusion is a continuous process of manufacturing of composite materials whereby fibers are pulled first through a resin bath and afterwards through a heated die, where the resin undergoes polymerization. Thus, the pultrusion technique results in a bundle of filaments or fibers being impregnated with a resin that is hardened by polymerization/crosslinking after being applied onto the fibers.

Since pultrusion impregnation only results in a thickness of the outer resin layer of about 0.1 mm, subsequent modifications of the surface of such posts is hampered. Mechanical modification of the surface by e.g. sand or glass bead blasting, fine sand paper roughening, grinding or the like frequently results in the central filaments or fibers being exposed.

Frequently used fibers or filaments such as Nylon® or glass are relatively hydrophilic. However, hydrophilic surface parts are believed to be disadvantageous since this may result in accelerated water aging of the post, in vitro hydrolytic degradation as an extreme scenario, especially at the fiber/resin interface. Thus, desirous flexibility in providing surface modifications and textures on the surfaces are hampered by the risk of exposing or even damaging the fibers/filaments.

Accordingly, it is an object of the present invention to overcome the drawbacks of the prior art, especially to provide an efficient method of producing dental posts, while at the same time both avoiding exposure and/or damage of inner fibers/filaments, and making surface modifications of the post more easily and reliably achievable.

The above object is solved by a method of manufacturing a dental post, and a dental post obtainable by such method, according to the independent claims.

A method of manufacturing a dental post according to the present invention comprises the steps of:
(i) overjacketing extrusion of at least one thermoplastic material over at least one filament or yarn, such that the thermoplastic material, in cross-section, enwraps the at least one filament or yarn;
(ii) solidifying the extruded product of step (i);
(iii) equipping the solidified extruded product of step (ii) with a surface texture, such that the thermoplastic wrapping is not modified in a way as to expose or damage the at least one filament or yarn.

Overjacketing extrusion, as understood herein, is a coating process, wherein a core material that is either non-thermoplastic or held at a temperature below its glass transition temperature $T_g$, such as a fibre, filament, or the like (or bundles of fibres, filaments, or the like) is pulled through the extrusion die, and at least one thermoplastic material is extruded around said core material.

Dental post, as used herein, also comprises dental pins.

There are two different types of extrusion tooling used for such coating. They are commonly referred to as either "pressure" or "jacketing" tooling. The selection criteria for choosing which type of tooling to use is based on whether the particular application requires intimate contact or adhesion of the polymer to the wire or not. If intimate contact or adhesion is required, pressure tooling is used. If it is not desired, jacketing tooling is chosen. In principle, both methods can be used in the context of the present invention; however, pressure tooling is preferred for reasons of reliability and durability of the resulting posts, especially in view of potential hydrophilic effects at the interface of the different materials of the posts, as outlined above.

In contrast to the pultrusion technique outlined in the introductory part, overjacketing extrusion of a thermoplastic material over at least one filament or yarn easily allows for the generation of an outer layer of thermoplastic material in almost any desired thickness.

Solidifying of the extruded product in step (ii) can be easily achieved by mere cooling of the thermoplastic material so that substantial flow is prevented; preferably, solidifying is achieved by (actively or passively) cooling the thermoplastic material to a temperature below its glass transition temperature $T_g$. If desired for certain embodiments, the thermoplastic material may be chosen such as to allow for subsequent further crosslinking or polymerization. Thereby, a dental post with a not thermoplastic coating can be achieved, albeit taking advantage of the thermoplastic properties of the raw material during the extrusion process.

Overjacketing extrusion efficiently avoids the inherent disadvantage of very thin impregnation by a pultrusion technique, while at the same time still allowing for a continuous process. The layer of the thermoplastic material can easily be dimensioned by the person of routine skill in the art by mere choice of the suitable die. Having provided a layer of the thermoplastic material in an appropriate thickness in an overjacketing extrusion process as outlined above, the layer of thermoplastic material can be easily equipped with a desired surface texture by either conventional techniques such as grinding, sand or glass bead blasting, fine sand paper roughening, or the like; or, preferably, by thermal (re-)shaping of the thermoplastic material. Towards this end, e.g. suitable molds can be used, thus easily allowing for even complex surface textures being generated by mere directed heating.

The surface texture generated in step (iii) may be of any suitable size and shape aiding in handling and/or fitting/retaining in the root canal. Typical surface textures are e.g. lengthwise grooves, e.g. parallel to or wound around the central axis of the post, interconnected or isolated; circumferential grooves, either at a right angle to the central axis of the post or tilted to central axis of the post, interconnected or isolated; undercuts.

According to a preferred embodiment, overjacketing extrusion in step (i) is carried out such that the extruded product is of substantially cylindrical shape, preferably of substantially circular-cylindrical or substantially elliptic-cylindrical shape. This can be easily achieved by carrying out the extrusion process through a substantially circular or elliptic die, as is known in the art or extrusion. Of course, due to the extrusion process, any desired lengthwise texture on the surface can immediately be generated during the extrusion. E.g., lengthwise grooves on the surface may be generated with a suitable die, allowing for venting excess bonding material (e.g. cement) when the post is fixed in the root channel, and preventing rotation of the post once the bonding material is hardened.

The diameter of the central filament(s) and/or yarn(s) typically is in the range of about 0.3 mm to about 2.5 mm, more preferably in the range of about 0.5 mm to about 2.0 mm. In most cases, the purpose of the central filament is to provide sufficient strength for the dental post. Therefore, the diameter of the central filament will be dictated in each case by the desired properties of the post employed. The person of routine skill in the art will readily realize necessary diameters, based on these considerations and, if necessary, routine experiments.

Moreover, a multitude, e.g. a bundle of filament(s) and/or yarn(s) can be used in step (i). For example, filaments and/or fibers can be wound around a central filament or yarn, as is generally known in the art (cf e.g. DE 39 01 640 A1, incorporated herein by reference). Also braided fibers and/or filaments can be used in the context of the present invention, such as e.g. disclosed in U.S. Pat. No. 6,402,519 B1, incorporated herein by reference).

In further embodiments of the present invention, the material of the filament(s) and/or yarn(s) is/are chosen from the group consisting ceramic; carbon; graphite; Alumina/Silica/Boria composites such as Nextel® 312, Nextel® 440; $Al_2O_3$; quartz; glass such as e.g. alkali resistant glass (preferably comprising $ZrO_2$), glass with high tensile strength (e.g. S-2 glass); $SiO_2$; Kevlar; metal; plastics such as e.g. acrylonitrile butadiene styrene (ABS), polyamide (PA), polyacrylates such as e.g. polymethylmethacrylate (PMMA) and polymethacrylate (PMA), polyetherketones (PEK), polyetheretherketones (PEEK), polysulfones (PS), polyethersulfones (PES), polyphenylenes, Polycarbonate (PC), polyethylene terephthalate (PET), polyethylene (PE), polypropylene (PP), polystyrene (PS), Polyvinylchloride (PVC); Liquid Crystal Polymer (LCP), Polyacetal (POM or Acetal), Polyacrylonitrile (PAN or Acrylonitrile), Polyamideimide (PAI), Polyaryletherketone (PAEK or Ketone), Polybutylene terephthalate (PBT), Polycaprolactone (PCL), Polychlorotrifluoroethylene (PCTFE), Polyethylene terephthalate (PET), Polycyclohexylene dimethylene terephthalate (PCT), Polyhydroxyalkanoates (PHAs), Polyketone (PK), Polyester, Polyetherimide (PEI), Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polystyrene (PS), Polysulfone (PSU), Polyurethane (PU), Polyvinyl acetate (PVA), Polyvinyl chloride (PVC), Polyvinylidene chloride (PVDC), Styrene-acrylonitrile (SAN); and combinations thereof.

If radio-opacity of the post is desired, the filament(s) or fiber(s) can be made of or may comprise metal. If metals are not desired for the risk of galvanic currents and the relatively high elastic modulus, other radio-opaque materials can be used, as will be readily realized by the person of routine skill in the art. For example, zirconium dioxide (zirconia) or barium glass can be incorporated into the filament(s) or fiber (s) in order to achieve radio-opacity, as is known from e.g. EP 992 223 B1 (incorporated herein by reference).

Of course, suitable radio-opaque additives can also be incorporated into other parts of the post, especially into the thermoplastic material. Suitable radio-opaque additives are well known in the art of dentistry, and can be chosen with ease by the person of routine skill in the art. Oxides of Zr, Ba, Sr and Zn are applicable, as well as fluorides of Yb and Y. Dental glass can also be used in this respect, especially comprising at least one of the aforementioned oxides. Currently, the preferred additive zirconium dioxide.

According to preferred embodiments, the thermoplastic material(s) in step (i) is/are chosen from the group consisting of acrylonitrile butadiene styrene (ABS), polyamide (PA), polyacrylates such as e.g. polymethylmethacrylate (PMMA) and polymethacrylate (PMA), polyetherketones (PEK), polyetheretherketones (PEEK), polysulfones (PS), polyethersulfones (PES), polyphenylenes, Polycarbonate (PC), polyethylene terephthalate (PET), polyethylene (PE), polypropylene (PP), polystyrene (PS), Polyvinylchloride (PVC); Liquid Crystal Polymer (LCP), Polyacetal (POM or Acetal), Polyacrylonitrile (PAN or Acrylonitrile), Polyamideimide (PAI), Polyaryletherketone (PAEK or Ketone), Polybutylene terephthalate (PBT), Polycaprolactone (PCL), Polychlorotrifluoroethylene (PCTFE), Polyethylene terephthalate (PET), Polycyclohexylene dimethylene terephthalate (PCT), Polyhydroxyalkanoates (PHAs), Polyketone (PK), Polyester, Polyetherimide (PEI), Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polystyrene (PS), Polysulfone (PSU), Polyurethane (PU), Polyvinyl acetate (PVA), Polyvinyl chloride (PVC), Polyvinylidene chloride (PVDC), Styrene-acrylonitrile (SAN), and mixtures thereof.

Most efficiently, the overjacketing extrusion will be carried out in a continuous process. Thus, in preferred embodiments, the extruded product is cut to length after step (i), preferably after step (ii) or step (iii), by any means known in the art. The extruded product can e.g. be cut to length with a suitable shear edge tool.

In order to avoid the risk of hydrophilic degradation outlined above, at least the cut surfaces are treated in preferred embodiments such that substantially no filament and/or yarn is exposed. This can be achieved most easily by thermal reshaping of the respective cut surface above the glass transition temperature of the thermoplastic material, such that the thermoplastic material flows over the cut surface to cover the filament and/or yarn.

According to yet further preferred embodiments, the solidified extruded product is equipped, partially or in total, with a further outer layer of thermoplastic material. This layer can be made or can comprise the same thermoplastic material as the one used in the overjacketing extrusion step. Preferably, this additional outer layer of thermoplastic material is applied by injection molding. The surface texture can be produced in step (iii) in this outer layer of thermoplastic material very efficiently, since the mold can be provided with any desired texture, the replica of which texture will be the surface texture of the dental post. Of course, the suchlike produced surface texture may reach into the layer of thermoplastic material generated in the overjacketing extrusion step (i).

According to a further preferred embodiment, the dental post is made of a fiber or filament which is radio-opaque (preferably glass containing zirconium dioxide in order to allow for radio-opacity) enwrapped with thermoplastic material, wherein the difference between the refraction index of the fiber or filament and the thermoplastic material is less than 0.15. This allows for providing radio-opaque posts that are transparent, as is discussed in any detail in EP 1 115 349 B1 (incorporated herein by reference).

As outlined above, any desired surface texture can be produced by directed thermal shaping and/or re-shaping of thermoplastic material. For the avoidance of doubt, this at least can be done by (a) shaping of a thermoplastic material already during extrusion in step (i); (b) thermal re-shaping of such thermoplastic extruded material of step (i); (c) thermal shaping of an additional thermoplastic material subsequently applied onto the extruded product of step (i); and (d) thermal re-shaping of such an additional thermoplastic material subsequently applied onto the product of step (i). In any case, if desired, a surface texture may be applied with any mechanical means known in the art such as grinding, sanding, etc., either in combination with or without thermal (re-)shaping as outlined above.

Yet another aspect of the present invention thus concerns a dental post, obtainable by a method as set forth above. According to the method of the present invention, dental posts are achievable that could not be produced by the prior art methods, e.g. by pultrusion. The at least one layer of thermoplastic material is geometrically very uniform in lengthwise direction, which is an inherent feature of the extrusion process. Moreover, a thickness of the thermoplastic layer in the range of about 0.01 mm to about 1.0 mm, preferably about 0.03 to about 0.7 mm, most preferably about 0.05 to about 0.5 mm is easily achievable. In contrast, with the pultrusion technique, such layer thickness cannot routinely be obtained.

A further aspect of the present invention concerns a dental post, with at least an inner and least an outer layer of thermoplastic material over at least one filament or yarn, such that thermoplastic material, in cross-section, enwraps the at least one filament or yarn. A surface texture can be provided in the outer layer of thermoplastic material, and may but need not reach into the inner layer of thermoplastic material.

In preferred embodiments, a dental post has the following dimensions:
- a length in the range of about 5 mm to about 40 mm, preferably about 8 to about 30 mm, most preferably about 10 to about 25 mm;
- a maximum cross-sectional diameter in the range of about 0.5 mm to about 3 mm, preferably about 0.7 to about 2.5 mm, most preferably about 0.8 to about 2.0 mm.

Yet another aspect of the present invention pertains to the use of at least one thermoplastic material for modifying the surface properties of a dental post. Mechanical properties of the dental post such as stiffness, strength, etc. are mainly dictated by the inner filament(s) and/or fiber(s). An outer layer of a thermoplastic material is, due to its thermoplasticity, easily applicable. This opens up new options in manufacture of such dental posts. For example, a green body can be produced, already comprising the inner filament(s) and/or yarn(s), and the extruded layer of thermoplastic material. From this single green body, a multitude of subsequent processing is possible, depending only on the desired properties of the resulting post. The green body can e.g. be equipped with yet another layer of thermoplastic material by injection molding, and a surface texture can be provided in the another layer of thermoplastic material with a suitable mold. Moreover, by appropriately choosing the outer thermoplastic material, special surface properties can be easily achieved, e.g. properties that enhance bonding to the tooth and/or the bonding agent such as a cement. Or, the green body is directly provided with a surface structure by thermal (re-)shaping of the thermoplastic layer formed in the extrusion process.

Figure 2:
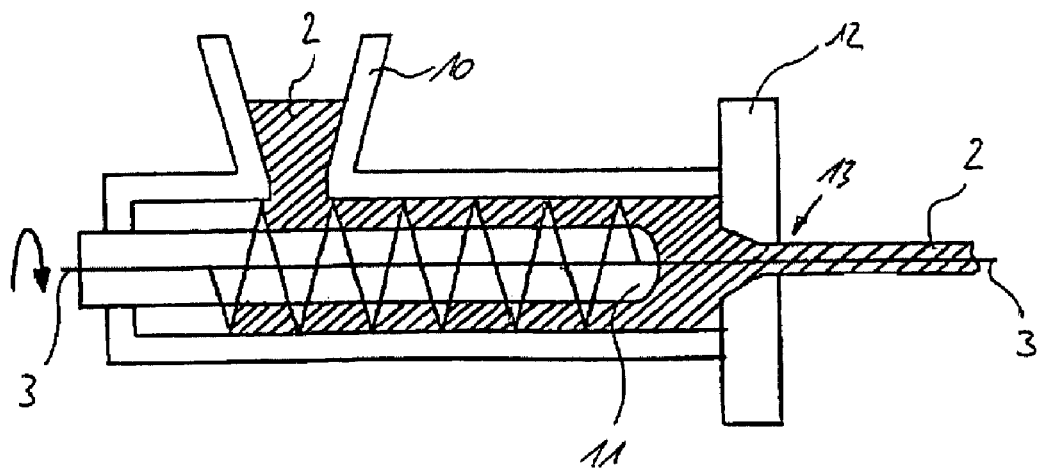
Figure 3:
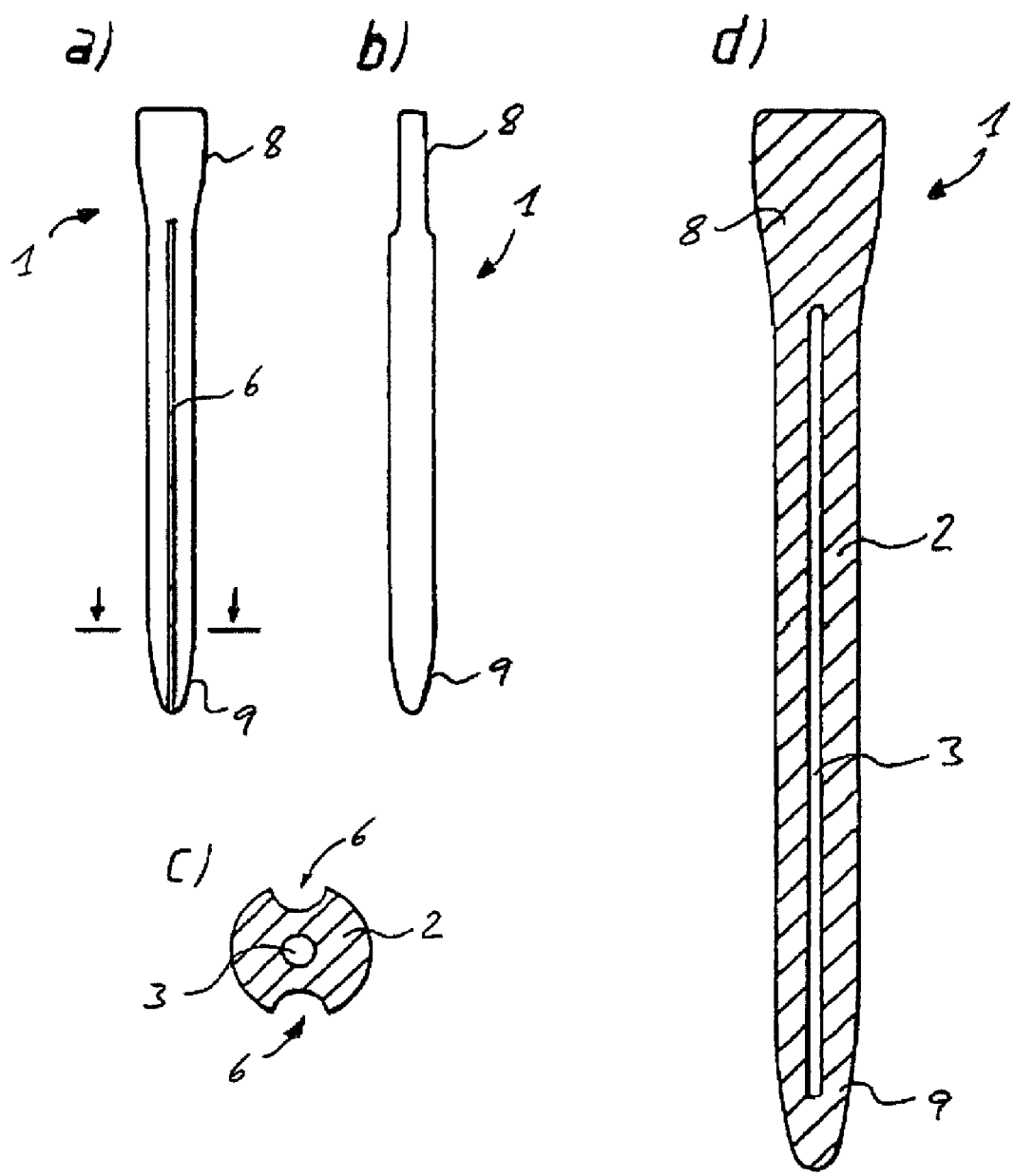
Figure 4:
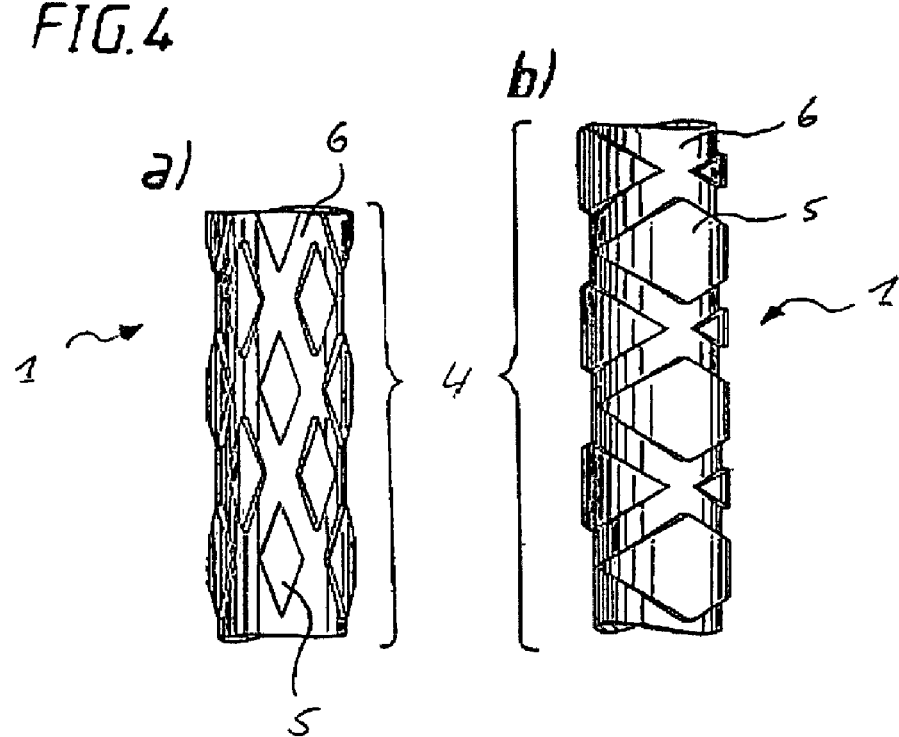
Figure 5:
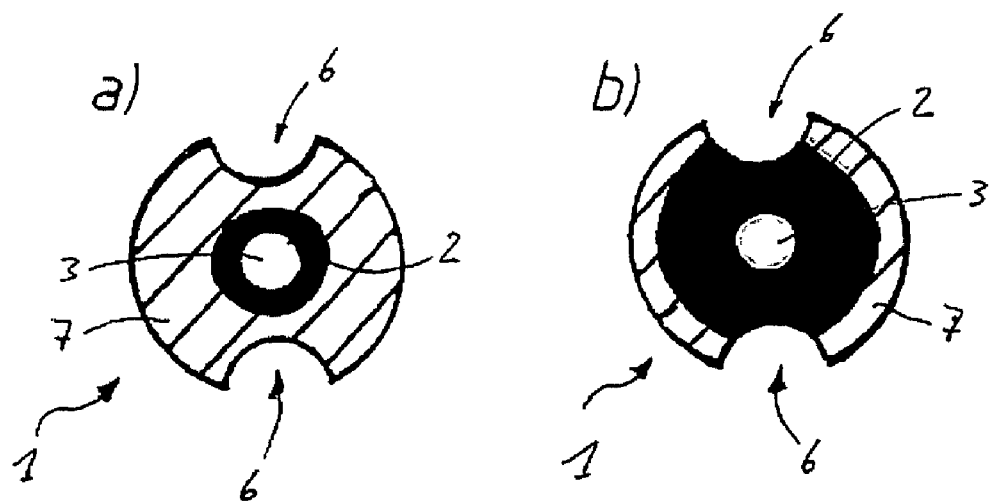

The invention will now be described in even more detail, by means of preferred embodiments, without however limiting the scope of the invention to these embodiments. The figures schematically show:

FIG. 1: Tooth;
FIG. 2: Overjacketing extrusion process;
FIG. 3: Dental post:
a) side view, lengthwise;
b) side view, lengthwise, rotated 90° around the central axis in comparison to a);
c) cross section, as indicated in a);
d) cross section, the dental post lengthwise cut in half;
FIG. 4: Dental post, partial view:
a) surface texture;
b) alternative surface structure;
FIG. 5: Dental post, cross sectional view (as indicated in FIG. 3 a):
a) surface texture (recess) in an outer layer of thermoplastic material, not reaching into an inner layer of thermoplastic material;
b) surface texture (recess) in an outer layer of thermoplastic material, reaching into an inner layer of thermoplastic material.

FIG. 1 schematically illustrates a tooth T. The outer layer of the tooth is called enamel E, the layer underneath is commonly referred to as dentin D. The most inner part of the tooth is the pulp P that also extends into the root canal. The pulp comprises blood vessels V and nerves N, that reach through the root. The tooth T is moreover embedded into gum G and the bone B.

FIG. 2 is a simplified illustration of an overjacketing extrusion process that can be used in the method according to the present invention. An extruder comprises a hopper 10, into which the thermoplastic material 2 is fed, mostly in the form of pellets. The pellets reach the screw 11 of the extruder, and the thermoplastic material is conveyed under pressure and elevated temperature by the screw 11. Thereby, the thermoplastic material 2 is heated at a temperature above its glass transition temperature, and is then pressed through a beaker plate 12 and a die 13. In an overjacketing extrusion process, an inner material is to be coated by the extruded thermoplastic material 2. This can e.g. be achieved such that the inner material (here: a filament or yarn 3) is conveyed through the interior of the screw 11, which screw 11 thus is a hollow shaft. The filament or yarn 3 is released from the screw into the flowable thermoplastic material 2 right before the composite of thermoplastic material 2 and filament or yarn 3 passes the beaker plate and the die. The extruded composite of filament or yarn 3 and thermoplastic material can then be cut to length, and treated further in a manner as outlined above.

FIG. 3 illustrates dental posts that can be obtained by the method of the present invention. FIG. 3 a) shows a dental post 1, with a head portion 8 (to be used for stabilizing subsequent dental restoration) and a bottom portion 9 (for extending into the root canal), and with a surface texture in the form of a recess 6 (here: a groove parallel to lengthwise axis). The recess 6 (groove) allows for excessive bonding material to be released from the root canal upon inserting the dental post. FIG. 3 b) is a side view, lengthwise, rotated 90° around the central axis in comparison to a). The head portion 8, in this embodiment, is flat; however, the head portion 8 can of course be made in a different geometry, such as e.g. spherical. FIG. 3 c) is a cross-section across the plane indicated in FIG. 3 a), illustrating the inner positioning of the filament or yarn 3 and the recesses 6 (grooves) in the thermoplastic material 2. FIG. 3 d) is an illustration of the dental post in cross section, the dental post being cut in half lengthwise. Again, the head portion 8 and the bottom portion 9 can be seen. The inner filament or yarn 3 is not exposed but completely wrapped by the thermoplastic material. Thereby, hydrophilic degradation as outlined above is prevented. The head portion 8 and bottom portion 9 of the dental post 1 need are modified after the extrusion and cut to length, in order to enwrap the filament or yarn, as outlined above in any detail, e.g. with a shear edge tool, by mere thermal re-shaping of the thermoplastic material 2 in the head portion 8 and the bottom portion 9, or by subsequent injection molding with yet another thermoplastic material, which can be the same as the thermoplastic material 2 or a different one.

FIGS. 4 a) and b) depict typical surface textures 4, which are well known in the art as such. Here, the surface textures 4 comprise interconnected recesses 6 and isolated elevations 5. These surface textures can be easily achieved by thermal shaping or re-shaping of a thermoplastic material in a subsequent injection molding process. Even more complicated surface textures such as e.g. undercuts are easily achievable by such injection molding.

FIG. 5 illustrates again a cross section through the dental post 1 across the plane indicated in FIG. 3 a). In both embodiments a) and b) of FIG. 5, two thermoplastic materials have been used: An inner layer of a thermoplastic material 2 is built up on the central filament or yarn 3 in the overjacketing extrusion process. Next, yet another thermoplastic material 7 is applied onto this extruded product. Both embodiments carry recesses 6, as outlined above. As is readily apparent, the extruded layer of thermoplastic material 2 is relatively thin in FIG. 5 a), thus allowing for subsequent built-up of a relatively thick outer layer of yet another thermoplastic material 7. Thereby, the surface texture such as a recess 6 can be easily configured such as to not reach into the inner layer of thermoplastic material 2. In contrast, the extruded layer of thermoplastic material 2 is relatively thick in FIG. 5 b), thus only allowing for subsequent built-up of a relatively thin outer layer of yet another thermoplastic material 7. Thereby, a surface texture such as a recess 6 can be easily configured such as to reach into the inner layer or thermoplastic material 2. In any case, as outlined above, the thermoplastic materials 2 and 7 can be the same or different ones.

The invention claimed is:

1. A method of manufacturing a dental post, comprising the steps of:
   (i) overjacketing extrusion of at least one thermoplastic material over at least one filament or yarn, such that the thermoplastic material, in cross-section, enwraps the at least one filament yarn;
   (ii) solidifying the extruded product of step (i);
   (iii) equipping the solidified extruded product of step (ii) with a surface texture, such that the thermoplastic wrapping is not modified in a way as to expose or damage the at least one filament or yarn; and
   (iv) cutting the extruded product to length;
   wherein at least the cut surfaces are treated such that substantially no filament and/or yarn is exposed.

2. A method of manufacturing a dental post, comprising the steps of:
   (i) overjacketing extrusion of at least one thermoplastic material over at least one filament or yarn, such that the thermoplastic material, in cross-section, enwraps the at least one filament yarn;
   (ii) solidifying the extruded product of step (i);
   (iii) equipping the solidified extruded product of step (ii) with a surface texture, such that the thermoplastic wrapping is not modified in a way as to expose or damage the at least one filament or yarn;
   wherein the solidified extruded product is equipped, partially or in total, with a further outer layer of thermoplastic material; and
   wherein the outer layer of thermoplastic material is applied by injection molding.

* * * * *